United States Patent
Lee (10) Patent No.: US 10,251,732 B2
(45) Date of Patent: Apr. 9, 2019

(54) METHOD OF MANUFACTURING SCAFFOLD FOR TREATMENT OF TOOTH EXTRACTION SOCKET AND IMPLANTATION OF DENTAL IMPLANT

(71) Applicant: THE CATHOLIC UNIVERSITY OF KOREA INDUSTRY-ACADEMIC COOPERATION FOUNDATION, Seoul (KR)

(72) Inventor: Sang Hwa Lee, Seoul (KR)

(73) Assignee: THE CATHOLIC UNIVERSITY OF KOREA INDUSTRY-ACADEMIC COOPERATION FOUNDATION, Seoul (KR)

(*) Notice: Subject to any disclaimer, the term of this patent is extended or adjusted under 35 U.S.C. 154(b) by 274 days.

(21) Appl. No.: 15/123,165

(22) PCT Filed: Jul. 7, 2016

(86) PCT No.: PCT/KR2016/007348
§ 371 (c)(1),
(2) Date: Sep. 1, 2016

(87) PCT Pub. No.: WO2017/007248
PCT Pub. Date: Jan. 12, 2017

(65) Prior Publication Data
US 2017/0007374 A1 Jan. 12, 2017

(30) Foreign Application Priority Data
Jul. 8, 2015 (KR) ........................ 10-2015-0097377

(51) Int. Cl.
G06F 17/50 (2006.01)
A61C 13/00 (2006.01)
(Continued)

(52) U.S. Cl.
CPC .......... *A61C 13/0019* (2013.01); *A61B 6/032* (2013.01); *A61B 6/14* (2013.01);
(Continued)

(58) Field of Classification Search
CPC ......... A61B 6/032; A61B 6/14; A61C 8/0036; A61C 13/0004; A61C 13/0019;
(Continued)

(56) References Cited

U.S. PATENT DOCUMENTS 7,174,282 B2 2/2007 Hollister et al.
9,149,346 B1 10/2015 Caldiero
(Continued)

FOREIGN PATENT DOCUMENTS

KR  10-2009-0124649 A  12/2009
KR     10-1527934 B1    6/2015

*Primary Examiner* — Leo B Tentoni
(74) *Attorney, Agent, or Firm* — Novick, Kim & Lee, PLLC; Sang Ho Lee (57) ABSTRACT

Provided is a technique of allowing a dental implant to be stably placed after extraction, to be accurately placed in a tooth extraction socket, and to be stably placed in the tooth extraction socket according to implantation position and angle. A method of manufacturing a scaffold for treatment of a tooth extraction socket and implantation of a dental implant includes receiving dental implantation information of dental CT data which is previously input via a terminal of a manager; manufacturing, by using a three-dimensional (3D) printer, a 3D model comprising alveolar bones and teeth, which are distinguished therebetween, based on a medical image file that is a medical image file (DICOM file) of the dental CT data; performing virtual tooth-extraction by removing, from the manufactured 3D model, a region corresponding to a tooth in a tooth-extraction target area; and manufacturing, by using the 3D printer, a scaffold to be placed in an actual tooth extraction socket according to a shape of a tooth extraction socket that exists in the manu-
(Continued)

factured 3D model as a result of the virtual tooth-extraction, wherein, when the scaffold is manufactured, image data of the scaffold is amended to allow a guide hole for implanting the dental implant to be formed in the scaffold based on the dental implantation information.

1 Claim, 5 Drawing Sheets (51) Int. Cl.
  *A61B 6/03* (2006.01)
  *A61B 6/14* (2006.01)
  *B29C 64/386* (2017.01)
  *B29C 64/112* (2017.01)
  *B29C 64/106* (2017.01)
  *A61C 8/00* (2006.01)

(52) U.S. Cl.
  CPC ........ *A61C 8/0036* (2013.01); *A61C 13/0004* (2013.01); *B29C 64/106* (2017.08); *B29C 64/112* (2017.08); *B29C 64/386* (2017.08)

(58) Field of Classification Search
  CPC ... B29C 64/106; B29C 64/112; B29C 64/386; G06F 17/50
  USPC .............................. 264/308; 700/119; 703/1
  See application file for complete search history.

(56) References Cited

U.S. PATENT DOCUMENTS

| | | |
|---|---|---|
| 2010/0203478 A1 | 8/2010 | Rubbert |
| 2012/0271418 A1 | 10/2012 | Hollister et al. |
| 2013/0144422 A1* | 6/2013 | Choi ...................... A61C 1/084 700/119 |
| 2013/0261677 A1 | 10/2013 | Bouduban |
| 2015/0025855 A1* | 1/2015 | Fisker ...................... G06F 17/50 703/1 |
| 2015/0202024 A1* | 7/2015 | Fisker ................ A61C 13/0004 703/1 X |
| 2015/0335400 A1 | 11/2015 | Mao |
| 2015/0359609 A1 | 12/2015 | Khan |
| 2016/0016362 A1 | 1/2016 | Kim et al. |
| 2017/0007406 A1 | 1/2017 | Cui et al. |

* cited by examiner

METHOD OF MANUFACTURING SCAFFOLD FOR TREATMENT OF TOOTH EXTRACTION SOCKET AND IMPLANTATION OF DENTAL IMPLANT

TECHNICAL FIELD

The present disclosure relates to a dental implantation technique using manufacture of a scaffold to be inserted into a tooth extraction socket after tooth-extraction to help treatment, and more particularly, to a technique of fast and accurately manufacturing a scaffold to be immediately placed after tooth extraction in a tooth extraction process and simultaneously enabling dental implantation.

BACKGROUND ART

Although a tooth extraction socket formed after tooth extraction is spontaneously cured, the tooth extraction socket causes a loss of a height and width of alveolar bone during a curing process. The loss highly influences following implantation of a dental implant and a prognosis thereof. Accordingly, various bone grafts and barrier membranes using techniques have been used to maintain the form of alveolar bone. In particular, the techniques have been used to preserve the form of alveolar bone by immediately implanting a dental implant and grafting bones as soon as a tooth is extracted in the anterior teeth area, and to reduce a treatment period.

However, when there is a loss of a veneer block bone due to lesions, external injuries, etc., it is difficult to fix bone grafts and a dental implant and a treatment period is prolonged.

In addition, when a dental implant is implanted into a tooth extraction socket, the dental implant is placed after implantation position and angle of the dental implant are determined. However, it is difficult to place the dental implant into the tooth extraction socket due to a loss of alveolar bone, etc., and it is very difficult to determine the implantation position and angle of the dental implant.

In this regard, Korean Patent Publication No 10-2009-0124649 discloses a technique of efficiently performing an implantation operation by simulating an implantation position of a dental implant by using an image of an oral cavity of a patient.

However, the conventional techniques are technically characterized in merely predicting an implantation position for an implantation operation without consideration of a tooth extraction socket, and thus, it is difficult to solve problems of an implantation operation due to the tooth extraction socket after tooth extraction.

DETAILED DESCRIPTION OF THE INVENTION

Technical Problem

The present disclosure provides a technique of safely and accurately placing a dental implant in a tooth extraction socket after extraction of a tooth, and simultaneously placing the dental implant safely in the tooth extraction socket according to implantation position and angle.

Technical Solution

According to a first embodiment of the present disclosure, there is provided a method of manufacturing a scaffold for treatment of a tooth extraction socket and implantation of a dental implant, the method including receiving dental implantation information of dental CT data which is previously input via a terminal of a manager; manufacturing, by using a three-dimensional (3D) printer, a 3D model including alveolar bones and teeth, which are distinguished therebetween, based on a medical image file that is a medical image file (DICOM file) of the dental CT data; performing virtual tooth-extraction by removing, from the manufactured 3D model, a region corresponding to a tooth in a tooth-extraction target area; and manufacturing, by using the 3D printer, a scaffold to be placed in an actual tooth extraction socket according to a shape of a tooth extraction socket that exists in the manufactured 3D model as a result of the virtual tooth-extraction, wherein, when the scaffold is manufactured, image data of the scaffold is amended to allow a guide hole for implanting the dental implant to be formed in the scaffold based on the dental implantation information.

According to a second embodiment of the present disclosure, there is provided a method of manufacturing a scaffold for treatment of a tooth extraction socket and implantation of a dental implant, the method including: receiving dental implantation information of dental CT data which is previously input via a terminal of a manager; manufacturing, by using a three-dimensional (3D) printer, a 3D model including alveolar bones and teeth, which are distinguished therebetween, based on a medical image file that is a medical image file (DICOM file) of the dental CT data; performing virtual tooth-extraction by removing, from the manufactured 3D model, a region corresponding to a tooth in a tooth-extraction target area; manufacturing, by using the 3D printer, a scaffold to be placed in an actual tooth extraction socket according to a shape of a tooth extraction socket that exists in the manufactured 3D model as a result of the virtual tooth-extraction; and forming a guide hole for implanting the dental implant in the scaffold, based on the dental implantation information.

According to a third embodiment of the present disclosure, there is provided a method of manufacturing a scaffold for treatment of a tooth extraction socket and implantation of a dental implant, the method including receiving, from a computerized tomography (CT) imaging apparatus, a medical image file that is a medical image file (DICOM file) of dental CT data, and dental implantation information that is previously input via a terminal of a manager; generating image data of a scaffold to be placed in the tooth extraction socket formed when a tooth in a tooth-extraction target area is extracted, by using a region corresponding to the tooth in the tooth-extraction target area in the medical image file; amending the generated image data of the scaffold so as to allow a guide hole for implanting the dental implant to be formed in the scaffold, based on the dental implantation information; and manufacturing a scaffold corresponding to the amended image data by using a three-dimensional (3D) printer.

According to a fourth embodiment of the present disclosure, there is provided a method of manufacturing a scaffold for treatment of a tooth extraction socket and implantation of a dental implant, the method including receiving, from a computerized tomography (CT) imaging apparatus, a medical image file that is a medical image file (DICOM file) of dental CT data, and dental implantation information that is previously input via a terminal of a manager; generating image data of a scaffold to be placed in the tooth extraction socket formed when a tooth in a tooth-extraction target area is extracted, by using a region corresponding to the tooth in the tooth-extraction target area in the medical image file;

manufacturing the scaffold corresponding to the generated image data by using a three-dimensional (3D) printer; and forming a guide hole for implanting the dental implant in the manufactured scaffold, based on the dental implantation information.

Advantages Effects of the Invention

According to the present embodiments, there is no need to directly extract a tooth, and when a scaffold that accurately corresponds to the shape of a tooth extraction socket is manufactured, before a tooth is directly extracted, by using a medical image file included in dental CT data, the scaffold is manufactured by forming a guide hole for implanting a dental implant in the scaffold according to implantation position and angle of the dental implant.

Accordingly, when it is difficult to implant a dental implant according to a tooth extraction socket formed after a patient's tooth is actually extracted, a dental implantation operation may be immediately, accurately, and easily performed after the tooth-extraction by manufacturing and placing a scaffold having a guide hole formed therein by exactly applying reflecting dental implantation information to have the scaffold accurately matched with the tooth extraction socket, and then implanting a dental implant.

BEST MODE

Hereinafter, a method of manufacturing a scaffold for treatment of a tooth extraction socket and implantation of a dental implant according to first through fourth embodiments of the present disclosure will now be described with reference to accompanying drawings.

For the purposes of promoting an understanding of the principles of the disclosure, well-known functions or constructions are not described in detail. It should be understood that embodiments described herein should be considered in a descriptive sense only and not for purposes of limitation. Descriptions of features or aspects within each embodiment should typically be considered as available for other similar features or aspects in other embodiments.

Throughout the specification, like reference numerals refer to like elements throughout and redundant descriptions thereof are not provided here.

Figure 1:
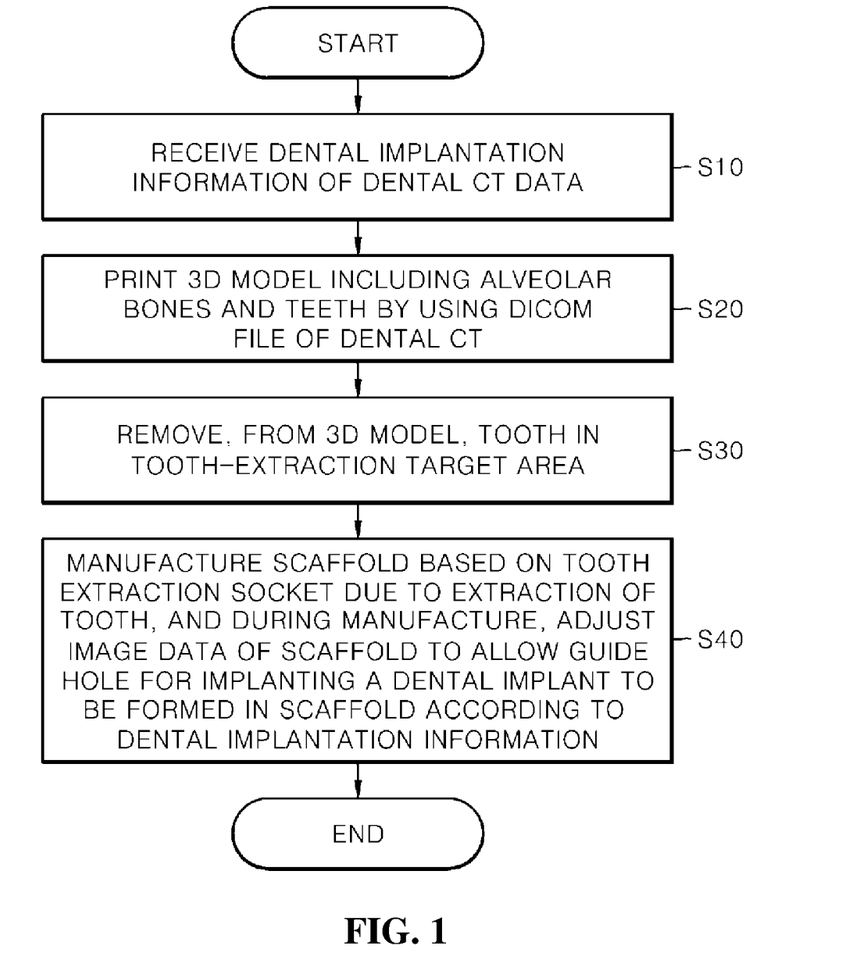
FIG. 1 is a flowchart of a method of manufacturing a scaffold for treatment of a tooth extraction socket and implantation of a dental implant, according to an embodiment.

FIG. 1 is a flowchart of a method of manufacturing a scaffold for treatment of a tooth extraction socket and implantation of a dental implant, according to an embodiment.

Referring to FIG. 1, the method of manufacturing a scaffold for treatment of a tooth extraction socket and implantation of a dental implant according to the present embodiment includes receiving dental implantation information of dental CT data, which is previously input via a terminal of a manager (a medical team) (operation S10)

The dental implantation information is one of a plurality of pieces of information that are input through the terminal of the medical team as the dental CT data, and means information, based on which the medical team determines a position of a dental implant. In more detail, the dental implantation information may include information regarding implantation position and angle of the dental implant. It is obvious that any information in addition to the aforementioned information may be included if the information is necessary for implantation of the dental implant.

After the operation S10 is performed, operation S20 is performed in which a three-dimensional (3D) model including alveolar bones and teeth, which are distinguished therebetween, is manufactured by using a 3D printer, based on a medical image file (digital imaging and communications in medicine (DICOM) file) of the dental CT data.

Dental CT is also referred to as cone beam computed tomography (CBCT) that is a scanner capable of scanning inside a tooth to be three-dimensionally recognizable. When a dental CT is performed by using a CT imaging apparatus, dental CT data is generated, and the data includes a medical image file (DICOM file) corresponding to a 3D image of the tooth.

The terminal of the manager receives the medical image file from the CT imaging apparatus, and a 3D printer connected to the terminal of the manager outputs and manufactures a 3D model corresponding to the medical image file.

In a medical image file that is generated as a CT imaging result, basically, clear white parts represent teeth, and less clear white parts such as soft white represent alveolar bones. Therefore, the alveolar bones may be distinguished from the teeth in the dental CT data of a patient, by using the medical image file.

When the 3D printer outputs a 3D model by using the medical image file, the 3D printer may output a 3D model where the alveolar bones are distinguished from the teeth to the extent that extraction of the teeth is available, so that the 3D printer may manufacture the 3D model according to the present embodiment. That is, in all embodiments of the present disclosure, a 3D model indicates a virtual object of a shape of an alveolar bone and tooth of a patient manufactured by using a 3D printer based on a medical image file.

When the operation S20 is performed and thus the 3D model is manufactured thereafter, operation S30 of performing virtual tooth-extraction by removing, from the 3D model, a region corresponding to a tooth in a tooth-extraction target area of a patient is performed.

To perform the virtual tooth-extraction in the 3D model means that the tooth is extracted not from an actual patient but from the object manufactured as the 3D model. The medical team determines a position of tooth-extraction based on the dental CT data, and then the operation S30 is performed by performing the tooth-extraction in the 3D model.

When the operation S30 is performed, the object in the 3D model is configured to have the extraction-target tooth extracted. As a result, a tooth extraction socket due to the extraction is formed in the 3D model. Afterward, operation S40 is performed so that a scaffold to be placed in an actual tooth extraction socket is manufactured by using the 3D printer, according to a shape of the tooth extraction socket that exists in the 3D model as the result of the virtual tooth-extraction, and in this regard, when the scaffold is manufactured, data of the scaffold is amended to allow a guide hole for implanting a dental implant to be formed in the scaffold, based on the dental implantation information received in the operation S10.

In more detail, in the operation S40, a 3D image of the scaffold to be manufactured may be generated according to the shape of the tooth extraction socket existing in the 3D model, the generated image may be amended to allow the guide hole to be formed in the scaffold, wherein the guide hole allows the dental implant to be implanted based on the dental implantation information, the amended image may be transmitted and requested for an output to the 3D printer, and then the scaffold may be manufactured by using the 3D printer.

For example, since the scaffold is manufactured by using a strip for a 3D printing output, the strip including bio-affinitive polymer (e.g., polycaprolactone (PCL)), it is possible to manufacture the bio-affinitive scaffold and to increase an effect on treatment.

After the scaffold is manufactured via the aforementioned procedure, additional operation of placing the scaffold in an actual tooth extraction socket of the patient may be performed. In this regard, when an alveolar bone of a scaffold placement target part is heavily absorbed, the scaffold may not be appropriately fixed.

In this case, the scaffold may be securely fixed to the alveolar bone by using a member such as a screw, or the like. The screw may be directly fixed to the scaffold placed at a grafting part or may be manufactured during the manufacture of the scaffold and then may be placed.

According to the flowchart, the virtual tooth-extraction may be performed on the 3D model that is duplicated to match the shape of the alveolar bone and tooth of the patient, and the scaffold may be manufactured by using the 3D printer so that the scaffold may be accurately implanted to match the shape of the tooth extraction socket formed due to the tooth-extraction, and even if it is impossible to securely implant the dental implant due to the loss of the alveolar bone or the like, the scaffold allows the dental implant to be securely and accurately implanted by using the guide hole.

Accordingly, without extracting an actual tooth of a patient, not a scaffold having a fixed shape and a typical dental implantation operation, but the scaffold that is securely fixable into a tooth extraction socket formed after extraction of an actual tooth of a patient may be manufactured regardless of the tooth extraction, and the dental implant may be immediately implanted during the placement of the scaffold. Accordingly, as soon as the actual tooth of the patient is extracted, the placement of the scaffold and implantation of the dental implant may fast and securely performed.

Figure 2:
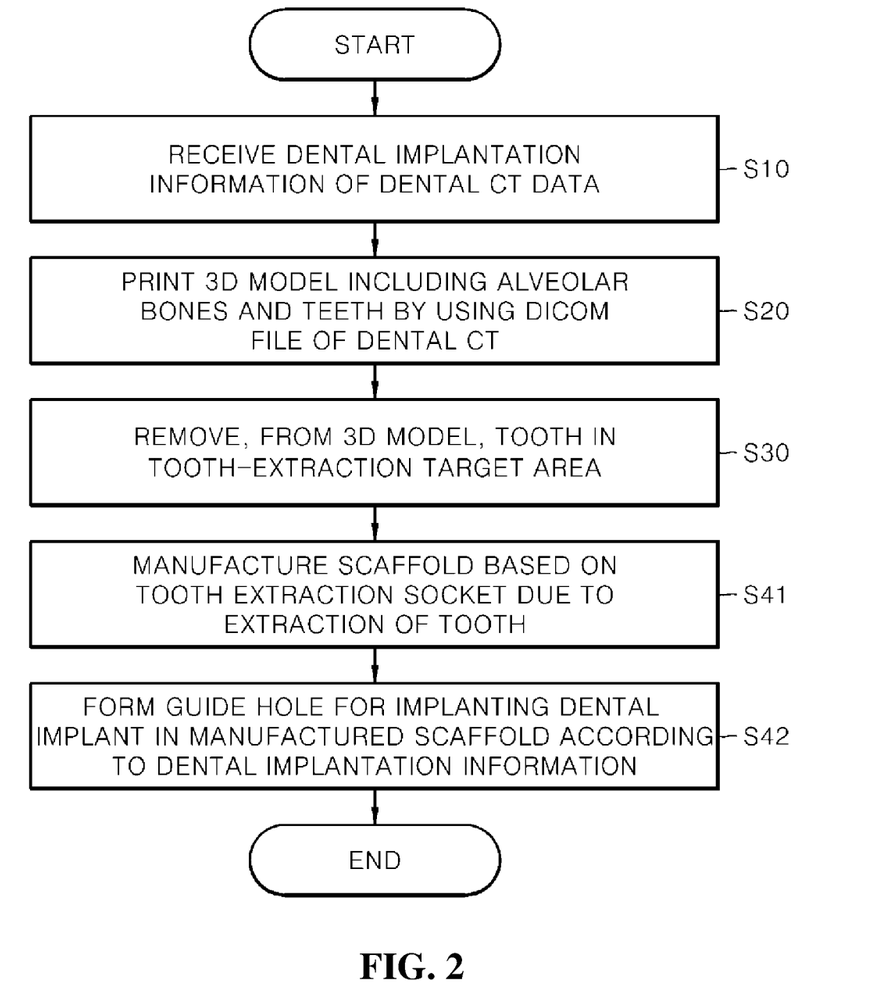
FIG. 2 is a flowchart of a method of manufacturing a scaffold for treatment of a tooth extraction socket and implantation of a dental implant, according to another embodiment.

FIG. 2 is a flowchart of a method of manufacturing a scaffold for treatment of a tooth extraction socket and implantation of a dental implant, according to another embodiment. Hereinafter, detailed descriptions, which are the same as the aforementioned contents of FIG. 1, will be omitted.

Referring to FIG. 2, the method of manufacturing a scaffold for treatment of a tooth extraction socket and implantation of a dental implant according to the present embodiment includes receiving dental implantation information of CT imaged data (operation S 10), printing a 3D model based on a medical image file of dental CT (operation S20), and virtually removing a tooth in a tooth-extraction target area (operation S30), as in the method of FIG. 1.

Afterward, unlike to that of FIG. 1, according to the present embodiment, operation S41 is performed in which a scaffold to be placed in an actual tooth extraction socket is manufactured by using a 3D printer according to a shape of a tooth extraction socket existing in the 3D model that is manufactured as a result of performing the virtual tooth-extraction in the operation S30. That is, unlike the operation S40 of FIG. 1, the scaffold to which the dental implantation information is not applied is manufactured according to the descriptions provided in the operation S40.

Afterward, operation S42 is performed in which a guide hole for implanting a dental implant is directly formed in the scaffold manufactured in the operation S41, based on the dental implantation information.

It is also possible to expect, via the operation S42, an effect of the embodiment described with reference to FIG. 1. In addition, a medical team may further precisely form the guide hole for implanting the dental implant while the medical team checks the manufactured scaffold.

Figure 3:
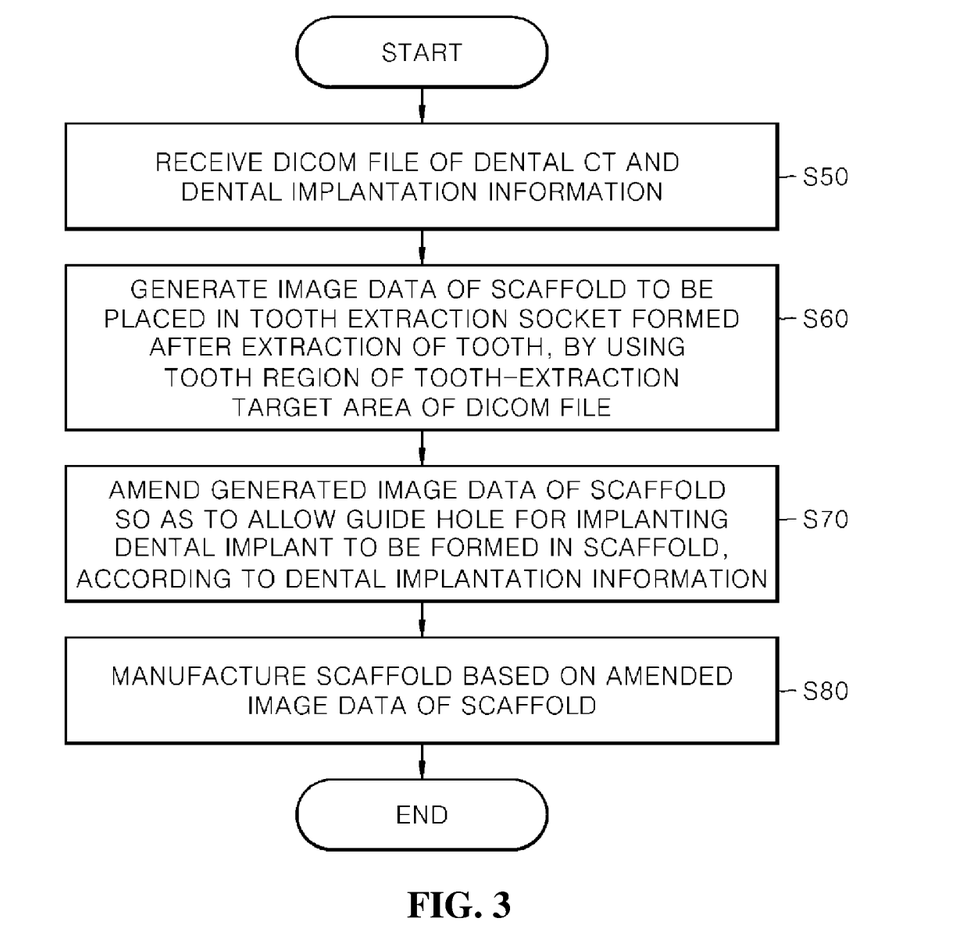
FIG. 3 is a flowchart of a method of manufacturing a scaffold for treatment of a tooth extraction socket and implantation of a dental implant, according to another embodiment.

FIG. 3 is a flowchart of a method of manufacturing a scaffold for treatment of a tooth extraction socket and implantation of a dental implant, according to another embodiment. Hereinafter, detailed descriptions, which are the same as the aforementioned contents of FIGS. 1 and 2, will be omitted.

Referring to FIG. 3, the method of manufacturing a scaffold for treatment of a tooth extraction socket and implantation of a dental implant according to the present embodiment includes receiving, from a CT imaging apparatus, dental implantation information, which was pre-input from the terminal of the manager, along with the medical image file of dental CT data (operation S50).

When the operation S50 is performed, unlike to the embodiments of FIGS. 1 and 2, operation S60 is performed in which image data of a scaffold that is fixable into a tooth extraction socket formed after extraction of a tooth in a tooth-extraction target area may be generated by using an image of a region of the received medical image file, wherein the region corresponds to the tooth in the tooth-extraction target area.

That is, referring to FIGS. 1 and 2, the 3D model corresponding to the medical image file is generated and then the image of the scaffold is generated therefrom, whereas in the third embodiment of FIG. 3, an image of the tooth extraction socket formed after the extraction is predicted from the medical image file, and the image data of the scaffold is generated therefrom.

In more detail, as described above, the image of the medical image file is configured in such a manner that the alveolar bones and the teeth are distinguished therebetween. In this regard, when the image corresponding to the region of the extraction-target tooth is removed, a shape of the tooth extraction socket to be formed thereof may be predicted, accordingly, the image data may be generated from the medical image file, wherein the image data includes data about a detailed shape of the scaffold that is fixable into the tooth extraction socket formed as a result of the tooth-extraction.

After the operation S60 is performed, operation S70 is performed in which the generated image data of the scaffold is amended to allow the aforementioned guide hole for implanting the dental implant to be formed in the scaffold, based on the dental implantation information.

Afterward, operation S80 is performed in which amended image data of the scaffold is transmitted to the 3D printer and then a scaffold corresponding to the amended image data of the scaffold is manufactured.

According to the third embodiment, similar to the first and second embodiments, the virtual tooth-extraction may be performed on the 3D model that is copied and manufactured to match with the shape of the alveolar bone and tooth of the patient, and the scaffold may be manufactured by using the 3D printer so that the scaffold may be accurately implanted to the shape of the tooth extraction socket formed due to the tooth-extraction, and even if it is impossible to securely implant the dental implant due to the loss of the alveolar bone or the like, the scaffold allows the dental implant to be securely and accurately implanted by using the guide hole.

Accordingly, without extracting an actual tooth of a patient, placement of a scaffold and dental implant is not uniformly performed, but the scaffold that is securely fixable into a tooth extraction socket formed after an actual tooth is extracted from the patient may be manufactured regardless of the extraction, and the dental implant may be immediately implanted during the placement of the scaffold, so that, as soon as the actual tooth is extracted from the patient, the placement of the scaffold and implantation of the dental implant may fast and securely performed.

Figure 4:
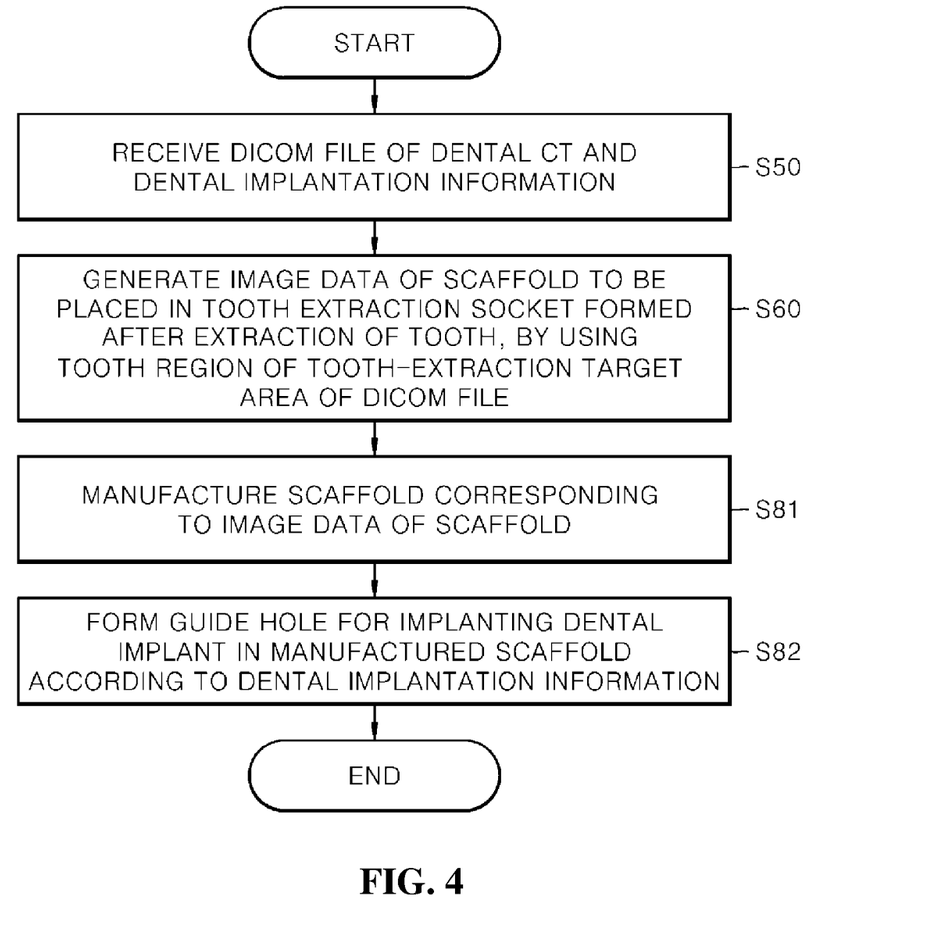
FIG. 4 is a flowchart of a method of manufacturing a scaffold for treatment of a tooth extraction socket and implantation of a dental implant, according to another embodiment.

FIG. 4 is a flowchart of a method of manufacturing a scaffold for treatment of a tooth extraction socket and implantation of a dental implant, according to another embodiment. Hereinafter, detailed descriptions, which are the same as the aforementioned contents of FIGS. 1 through 3, will be omitted.

Referring to FIG. 4, similar to the embodiment of FIG. 3, the method of manufacturing a scaffold for treatment of a tooth extraction socket and implantation of a dental implant according to the present embodiment includes receiving a medical image file of dental CT and dental implantation information (operation S50), and generating, from the medical image file, image data of a scaffold to be placed in a tooth extraction socket (operation S60).

Afterward, unlike to the embodiment of FIG. 3, operation S81 of manufacturing a scaffold corresponding to the image data of the scaffold by using the 3D printer is performed. That is, the operation S81 includes similar technical features as those of the operation S41 of FIG. 2.

When the operation S81 is performed and thus the scaffold is manufactured, similar to the operation S42 of FIG. 2, operation S82 is performed in which a guide hole for implanting a dental implant is directly formed in the scaffold, based on the dental implantation information. That is, the present embodiment described with reference to FIG. 4 is characterized in including the same technical features as the second embodiment of FIG. 2 with respect to forming the guide hole.

Figure 5:
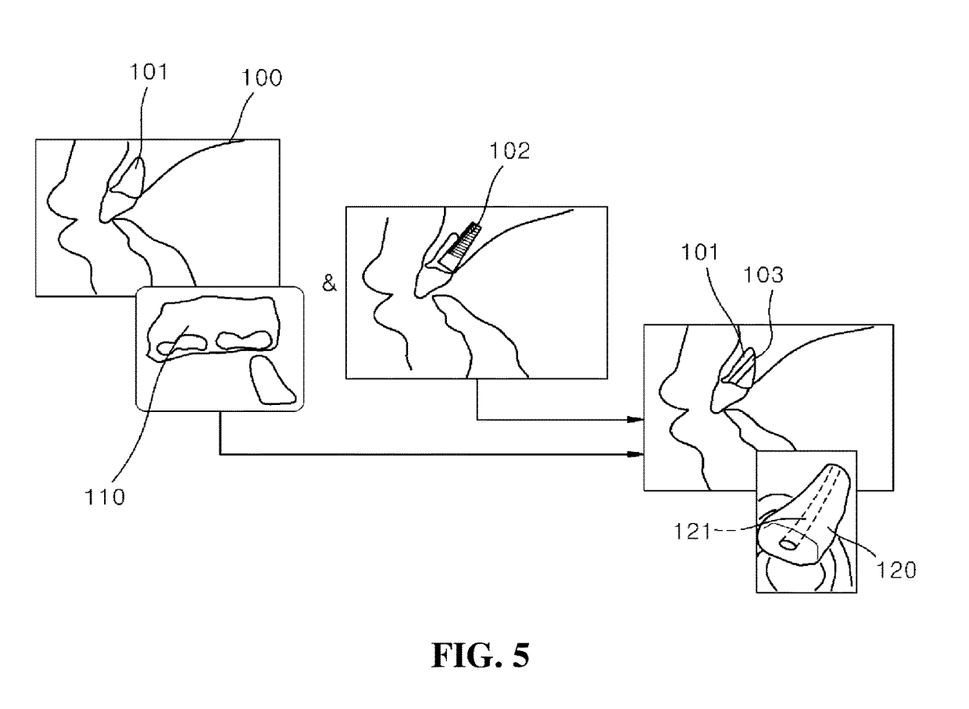
FIG. 5 illustrates a test example of manufacturing a scaffold for treatment of a tooth extraction socket and implantation of a dental implant, according to each of the embodiments.

FIG. 5 illustrates a test example of manufacturing a scaffold for treatment of a tooth extraction socket and implantation of a dental implant, according to each of the embodiments.

Referring to FIG. 5, a scaffold image data 101 is generated from a medical image file 100 of CT imaged data by performing functions described with reference to FIGS. 3 and 4. By doing so, a 3D model 110 may be manufactured.

Then, dental implantation information based on a virtual image 102 of a dental implant implanting means may be generated on the medical image file 100 and the CT imaged data.

The dental implantation information is applied to the scaffold image data 101 so that image data 103 with respect to a guide hole may be generated.

Various embodiments may be implemented, e.g., a guide hole 121 may be manufactured on a scaffold 120 based on this or the guide hole 121 may be directly formed in the pre-manufactured scaffold 120.

It will be apparent that all elements of the one or more embodiments of the present disclosure are not limited to be combined or to operate as one combination. That is, all elements may be selectively combined and may operate as one within the scope of the present disclosure.

In addition, when a part "includes", "comprises", "is configured of", or "has" an element, unless there is a particular description contrary thereto, the part can further include other elements, not excluding the other elements. Unless expressly described otherwise, all terms including descriptive or technical terms which are used herein should be construed as having meanings that are obvious to one of ordinary skill in the art. Also, terms that are defined in a general dictionary and that are used in the following description should be construed as having meanings that are equivalent to meanings used in the related description, and unless expressly described otherwise herein, the terms should not be construed as being ideal or excessively formal.

While the present disclosure has been particularly shown and described with reference to exemplary embodiments thereof, it will be understood by one of ordinary skill in the art that various changes in form and details may be made therein without departing from the spirit and scope of the following claims. Therefore, the scope of the present disclosure is defined not by the detailed description of the present disclosure but by the appended claims, and all differences within the scope will be construed as being included in the present disclosure.

The invention claimed is:

1. A method of manufacturing a scaffold for treatment of a tooth extraction socket and implantation of a dental implant, the method comprising:
   receiving, from a computerized tomography (CT) imaging apparatus, a medical image file that is a medical image file (DICOM file) of dental CT data, and dental implantation information that is previously input via a terminal, wherein the dental implantation information includes an implantation position and an angle of the dental implant;
   generating image data of the medical image file having an alveolar bone and a tooth, which are distinguished therebetween;
   removing an image region of the tooth from the image data;
   predicting a shape of the tooth extraction socket;
   generating a scaffold image to be placed in the tooth extraction socket;
   amending the scaffold image to have a virtual guide hole for implanting the dental implant based on the dental implantation information of the implantation position and the angle of the dental implant;
   manufacturing a scaffold corresponding to the scaffold image by using a three-dimensional (3D) printer to have a guide hole in reply to the virtual guide hole; and
   implanting the scaffold immediately after the tooth is extracted therefrom.

* * * * *